United States Patent [19]

Koeneman et al.

[11] Patent Number: 4,757,809

[45] Date of Patent: Jul. 19, 1988

[54] PIN CLAMP

[75] Inventors: James B. Koeneman, Mesa; Thomas M. Hansen, Phoenix; Mark Phillips, Mesa; Allan M. Weinstein, Paradise Valley, all of Ariz.

[73] Assignee: Orthotic Limited Partnership, Tempe, Ariz.

[21] Appl. No.: 828,051

[22] Filed: Feb. 10, 1986

Related U.S. Application Data

[63] Continuation-in-part of Ser. No. 791,222, Oct. 25, 1985, which is a continuation-in-part of Ser. No. 604,047, Apr. 26, 1984, Pat. No. 4,584,995.

[51] Int. Cl.$^4$ ............................................... A61F 5/04
[52] U.S. Cl. ............................ 128/92 Z; 128/92 ZW; 24/136 B; 248/316.2; 403/354; 403/374
[58] Field of Search ........... 128/92 V, 92 YE, 92 YF, 128/92 VZ, 92 ZK, 92 ZW, 92 ZY, 92 ZZ, 92 Z; 24/136 B, 136 R; 248/312, 316.2, 53; 403/290, 354, 374; 188/67; 339/92 R, 273 R, 92 M; 411/179

[56] References Cited

U.S. PATENT DOCUMENTS

| | | | |
|---|---|---|---|
| 1,730,619 | 10/1929 | Mitchell | 188/67 |
| 2,055,443 | 9/1936 | Jones | 411/179 |
| 2,080,802 | 5/1937 | Anderson . | |
| 2,238,869 | 4/1941 | Haynes | 128/92 ZZ |
| 2,371,519 | 3/1945 | Haynes . | |
| 2,398,915 | 4/1946 | Bell . | |
| 2,434,431 | 1/1948 | Pincock . | |
| 3,547,113 | 12/1970 | Swanson . | |
| 3,673,312 | 6/1972 | Vockroth | 24/136 R X |
| 3,866,607 | 2/1975 | Forsythe et al. . | |
| 3,877,424 | 4/1975 | Murray . | |
| 3,977,397 | 8/1976 | Kalnberz et al. . | |
| 3,999,418 | 12/1976 | Morell | 339/273 F X |
| 4,185,624 | 1/1980 | Gentile | 128/92 ZZ X |
| 4,244,360 | 1/1981 | Dohogne . | |
| 4,308,863 | 1/1982 | Fischer . | |
| 4,361,144 | 11/1982 | Slatis et al. . | |
| 4,365,624 | 12/1982 | Jaquet . | |
| 4,430,523 | 2/1984 | Hayes | 24/136 R X |
| 4,471,846 | 9/1984 | Mullenberg | 24/136 B X |
| 4,502,473 | 3/1985 | Harris et al. | 128/92 ZY X |

FOREIGN PATENT DOCUMENTS

| | | | |
|---|---|---|---|
| 2532539 | 6/1976 | Fed. Rep. of Germany . | |
| 2338692 | of 1977 | France | 128/92 YE |
| 2086231 | 5/1982 | United Kingdom . | |
| 770487 | 10/1980 | U.S.S.R. . | |
| 0984468 | of 1983 | U.S.S.R. | 128/92 ZW |

OTHER PUBLICATIONS

Howmedica, Inc. brochure, "The External Fixation System", pp. 1–32.
E. Y. Chao et al, *J. Biomechanics*, "Rigidity and Stress Analyses of External Fracture Fixation Devices-a Theoretical Approach", vol. 15, No. 12, pp. 971–982.
E. Y. S. Chao et al, *Finite Elements in Biomechanics*, "Biomechanical Analysis of External Fixation Devices for the Treatment of Open Bone Fractures", pp. 195–220.
Mears, Dana C., "External Skeletal Fixation", pp. 1–41.
Ace Medical brochure, "The Ace-Fischer Fixator", pp. 1–12.

*Primary Examiner*—Richard J. Apley
*Assistant Examiner*—David J. Bender
*Attorney, Agent, or Firm*—Wood, Herron & Evans

[57] ABSTRACT

A pin clamp particularly adapted for use in an external skeletal fixation device to clamp pins inserted in the distal segment and/or proximal segment of a fractured bone for positioning and immobilizing the bone segments to reduce the fracture. The pin clamp employs a wedge lock construction including a block having a tapered, hollow interior which receives a wedge element having opposed, tapered sidewalls connected to a slotted top wall. The pins are inserted between the sidewalls of the wedge element into the slot, and are clamped therebetween as the wedge element is moved into the block. A screw carried by the block threads into a bore in the top wall of the wedge element to move the wedge element in and out of the block. Both the block and wedge element are formed of a composite material and the sidewalls of the wedge element which contact the pins are preferably coated with a grit material having a high coefficient of friction.

10 Claims, 2 Drawing Sheets

PIN CLAMP

RELATED APPLICATIONS

This is a continuation-in-part of application Ser. No. 791,222, filed Oct. 25, 1985 and entitled "External Fixation Device", which is a continuation-in-part of Ser. No. 604,047, filed Apr. 26, 1984 and entitled "External Fixation Device", now U.S. Pat. No. 4,584,995.

BACKGROUND OF THE INVENTION

This invention relates generally to devices for the treatment of bone fractures, and, more particularly, to a pin clamping device particularly adapted for use in an external fixation device for positioning and immobilizing the distal segment and the proximal segment of a fractured bone to apply controlled distraction and compression to the fracture.

External skeleton fixation devices have been developed in recent years for the treatment of long bone fractures with substantial soft tissue involvement as an alternative to prior art internal fixation devices such as bone plates, and to replace prior art treatment methods such as immobilization of the affected limb using traction devices. External fixation devices generally comprise one or more pins secured to the distal segment and to the proximal segment of a fractured bone, which are adjustably connected by pin clamps to a frame located externally of the affected limb. Each pin has a threaded portion inserted into the cortical bone of the proximal or distal bone segment, and a smooth, clamping portion located exteriorly of the limb. Once the bone segments are aligned in the correct anatomical position with the pins in place, the clamping portion of the pins are secured to the frame of the external fixation device by the pin clamps to maintain the bone segments in position.

Prior art pin clamps for use in external fixation devices generally comprise a pair of clamping blocks having facing surfaces each formed with a number of spaced notches. The clamping blocks are secured together by screws or other fasteners so that the notches in their facing surfaces align to form annular passageways which receive and grip the clamping portion of the pins.

Prior art pin clamps of the type described above have several limitations. One limitation is that the normal force applied to the pins by the mating clamping blocks is dependent solely upon the force with which the screws mounting the clamping blocks together are tightened. If the screws are tightened too loosely, the pins can work free within the clamping blocks and allow the bone segments which they support to move out of position within the limb. In addition, many prior art clamping blocks engage only a relatively small portion of the length of the pins which further limits the gripping force applied to the pins.

In reducing a fracture of a long bone, a drill guide having the same number and spacing of passageways as the pin clamp is first placed against the limb so that the surgeon can use the passageways in the drill guide to drill holes in the bone segments. The pins are inserted into the guide holes made in both the proximal segment and the distal segment of the bone, and the drill guide is then removed. Once the pins are in place in the bone, the frame of the external fixation device is then positioned with respect to the limb so that the clamping portions of the pins are received within the pin clamps of the frame and clamped in place. It is often difficult to obtain accurate pin placement in this fashion, particularly where further adjustment of the position of the bone segments, and, in turn, the pins, is required to reduce the fracture after the frame is in place.

Another limitation of prior art pin clamps is that they do not permit manipulation of the pins relative thereto once the pins are received in the passageways of the pin clamps. Since the method of inserting pins into the bone segments described above may not result in precise pin placement, some adjustment of the pins relative to the pin clamps may be necessary in the event of misalignment, particularly if further reduction of the fracture is necessary after the frame is in place.

Additionally, even if the pins are properly aligned with the passageways of the pin clamps when the frame is in position, many surgeons prefer to manipulate the clamping end of the pins so that the threaded portion in the bone becomes wedged within the pre-drilled bores. This manipulation of the pins applies a force between the pins and bone, and, in addition to the threads of the pins, helps hold the pins in place in the bone. The annular passageways of prior art pin clamps do not permit such adjustment, which could result in loosening of the pins within the bone.

SUMMARY OF THE INVENTION

It is therefore among the objectives of this invention to provide a pin clamp particularly adapted for use in an external fixation device which applies high normal forces along a substantial length of the pin to firmly clamp the pin in place, which permits manipulation of the outwardly extending clamping portion of the pin in the event of misalignment of the pin, and which permits manipulation of the pin and attached bone segment to prevent loosening of the pin within the bone.

These objectives are accomplished in a pin clamp particularly adapted for use in an external fixation device to firmly clamp pins inserted in the distal and/or proximal segments of a fractured bone for positioning and immobilizing the bone segments to reduce the fracture.

In a presently preferred embodiment of this invention, the pin clamp includes a block having opposed sidewalls and endwalls connected to a top wall to form a hollow interior with an open bottom. The surface of each sidewall which faces inwardly within the hollow interior is formed with a taper so that the cross section of the hollow interior increases from the top wall downwardly. Preferably, the top wall of the block is formed with a central bore straddled by a pair of elongated slots which are each adapted to receive the clamping portion of one or more pins.

A wedge element is insertable within the hollow interior of the block toward the top wall to effect clamping of the retaining pins. The wedge element is formed with opposed sidewalls connected to a top wall. The outer surface of each sidewall is formed with the same wedge or taper angle as the inner surfaces of the block sidewalls to mate therewith. The top wall of the wedge element has essentially the same configuration as the top wall of the block, including a central bore having an insert formed with internal threads and a pair of elongated slots on either side of the bore which receive one or more pins.

In order to clamp pins within the pin clamp of this invention, the clamping portion of each pin is inserted into an elongated slots of the wedge element and an elongated slot of the block. In order to move the wedge element upwardly within the hollow interior of the block, a screw is inserted through the bore in the top wall of the block and into the threaded insert in the top wall of the wedge element. By turning the screw in one direction, the wedge element is drawn upwardly within the hollow interior of the block toward its top wall. As the wedge element moves upwardly within the block, the tapered sidewalls of the block urge the tapered sidewalls of the wedge element inwardly, toward one another, to exert a high normal force along a substantial portion of the length of the pins therebetween.

An important aspect of this invention is that the pins are movable within the elongated slots of both the wedge element and block to accommodate misalignment of the pins, and to permit a surgeon to manipulate the pins before the pins are locked in place. In contrast to prior art pin clamps, the elongated slots of the wedge element and block which receive the pins are smooth and allow for movement of the pins along their entire length.

In a presently preferred embodiment, the block and wedge element are formed of a woven or unidirectional fiber-reinforced material, such as glass or graphite fiber, impregnated with an epoxy matrix material. This material produces a pin clamp which is lightweight and yet very strong and durable. Preferably, the inner surfaces of the sidewalls of the wedge element which engage the pins are at least partially coated with a grit material such as silicon carbide having a high coefficient of friction. This enhances the frictional engagement between the wedge element and pins to help hold the pins in place. In one embodiment, such inner surfaces are parallel to one another along their entire length. In an alternative embodiment, a portion of the inner surfaces is stepped inwardly at the base of the sidewalls of the wedge element to provide a localized area of high normal force against the pins thereat.

In another aspect of this invention, the inner surfaces of the sidewalls of the wedge element which engage the pins are lined with an elastic, deformable material such as "Kevlar" felt impregnated with an epoxy matrix. "Kevlar" is a registered trademark of the E. I. duPont de Nemours Company. The Kevlar felt has a lower modulus of elasticity than the composite wedge element, and at least partially conforms to the outer surface of the pin to provide for greater frictional engagement therebetween. The Kevlar felt material may also be at least partially coated with a grit compound such as silicon carbide to further increase its frictional engagement with the pins.

The wedge or taper angle of the inner surfaces of the block sidewalls and outer surfaces of the wedge element sidewalls is preferably in the range of about 2° to 8°. The "wedge or taper angle" herein is the angle between the sidewalls of the block, or the sidewalls of the wedge element, which are identical. Most preferably, the combined taper angle of the sidewalls of both the block and wedge element is 3° so that the wedge element and block are self-locking. Wedge or taper angles within the preferred range which are less than 3° provide increased normal forces on the pins, if desired. As the taper angle increases from 3° within the preferred range, the normal force applied to the pins lessen. The wedge element and block are not self-locking at taper angles in excess of about 5°, but the wedge element is maintained within the block at such higher taper angles by the screw. Higher taper angles may be desirable in some instances to facilitate separation of the wedge element from the block to release the pins.

DESCRIPTION OF THE DRAWINGS

The structure, operation and advantages of a presently preferred embodiment of this invention will become further apparent upon consideration of the following description, taken in conjunction with the accompanying drawings, wherein.

DETAILED DESCRIPTION OF THE INVENTION

Figure 1:
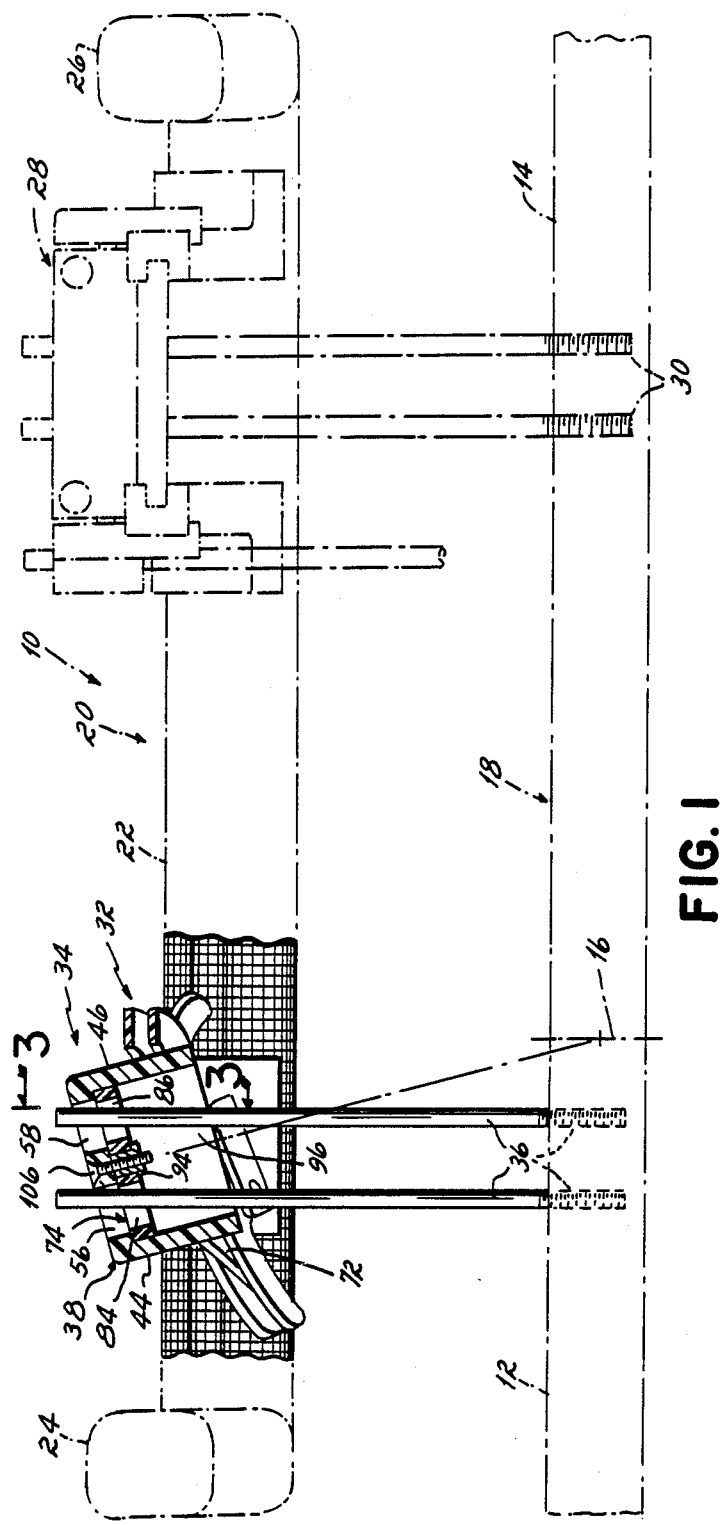
FIG. 1 is a partially schematic, side elevational view of an external fixation device incorporating the pin clamp of this invention to clamp half pins affixed within a segments of a fractured long bone.

Referring now to FIG. 1, an external fixation device 10 is schematically illustrated in a position to align the distal segment 12 and proximal segment 14 at the fracture 16 of a bone 18. The external fixation device 10 is discussed in detail in co-pending application Ser. No. 791,222, filed Oct. 25, 1985 and entitled "External Fixation Device", which is incorporated by reference in its entirety herein. Only a portion of the device 10 will be discussed herein for purposes of illustrating the invention.

The external fixation device 10 generally includes a frame 20 having opposed side rails 22, only one of which is illustrated in FIG. 1, connected at each end to a pair of end rails 24, 26. A proximal carriage 28, illustrated in phantom in FIG. 1, is mounted to the frame 20 and is adapted to clamp half pins 30 inserted within the proximal segment 14 of the bone 18. A distal carriage 32 is mounted to the opposite end of frame 20 and supports a pin clamp 34 which clamps half pins 36 inserted within the distal segment 12 of bone 18.

This invention is directed to the structure of pin clamp 34, which, as illustrated in FIG. 1, is mounted in the distal carriage 32 of the external fixation device 10. It should be understood that the pin clamp 34 could be employed in the proximal carriage 28, and it could also be adapted for use in external fixation devices of designs other than that illustrated in FIG. 1 and disclosed in the above-identified application Ser. No. 791,222 now U.S. Pat. No. 4,584,995. In addition, the pin clamp 34 is illustrated clamping half pins 30, 36, but it could also clamp other types of bone pins such as transcortical and transfixing pins.

The pin clamp 34 includes a block 38 having opposed sidewalls 40, 42, and opposed endwalls 44, 46, connected to a top wall 48 to define a hollow interior 50. In a presently preferred embodiment, the top wall 48 is formed with a bore 52 having a flanged recess at the top surface of top wall 48, and a pair of elongated slots 56, 58 on either side of the bore 52. The sidewalls 40, 42 have facing inner surfaces 60, 62, respectively, which taper outwardly relative to one another from the top wall 48 downwardly as viewed in FIGS. 2–4. The outer surfaces 64, 66 of sidewalls 40, 42 are each formed with flanges 68, 70 for mounting the pin clamp 34 to a cramping member 72 of distal carriage 32 as partially illustrated in FIG. 1.

Preferably, the wedge or taper angle of the inner surfaces 60, 62 of sidewalls 40, 42 is in the range of about 2° to 8°. The wedge or taper angle is the angle measured between the sidewalls 40, 42.

Figure 2:
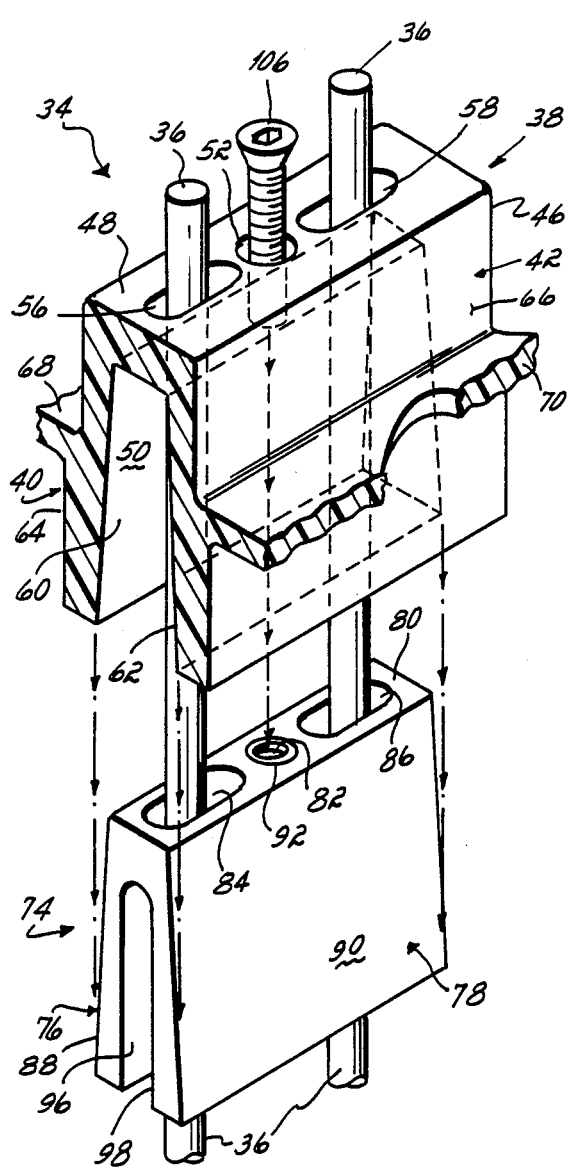
FIG. 2 is an exploded, isometric view in partial cross section of the pin clamp herein.

As best shown in FIG. 2, the pin clamp 34 includes a wedge element 74 insertable within the hollow interior 50 of block 38. The wedge element 74 comprises a pair of opposed sidewalls 76, 78 which are connected to a top wall 80 formed with a bore 82 and a pair of spaced, elongated slots 84, 86. Each of the sidewalls 76, 78 is formed with an outer surface 88, 90, respectively, which taper outwardly relative to one another from the top wall 80 downwardly as viewed in FIG. 2. The taper angle of the outer surfaces 88, 90 of sidewalls 76, 78 is identical to that of the block sidewalls 40, 42 so that the wedge element 74 mates with the block 38 upon insertion into its hollow interior 50. As illustrated in FIG. 1, the bore 82 formed in the top wall 80 of wedge element 74 receives a metal insert 92 having internal threads (not shown) and an annular flange 94 at its bottom edge which engages the bottom surface of top wall 80. The insert 92 is permanently attached to the top wall 80 by press fitting into bore 82 or by other suitable means of fixation.

Figure 3:
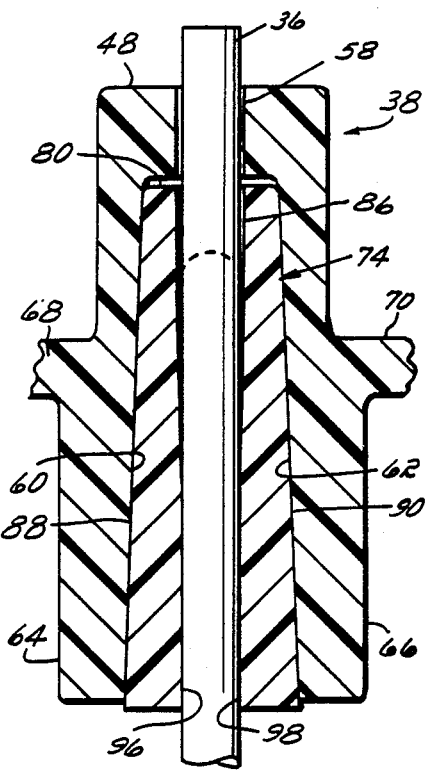
FIG. 3 is a partial cross sectional view taken generally along line 3—3 of FIG. 1 showing the half pin in a clamped position.

Each of the sidewalls 76, 78 of wedge element 74 is formed with an inner surface 96, 98, respectively, between which the half pins 36 are received for clamping. As shown in FIG. 3, in one embodiment of this invention the inner surfaces 96, 98 are substantially parallel to one another along their entire length. Alternatively, the inner surfaces 96, 98 are each formed with an inwardly extending, stepped portion 100, 102, respectively, near the base of sidewalls 76, 78. See FIG. 4. The stepped portions 100, 102 provide additional normal clamping force against the half pins 36, particularly at the base of the wedge element 74.

Figure 4:
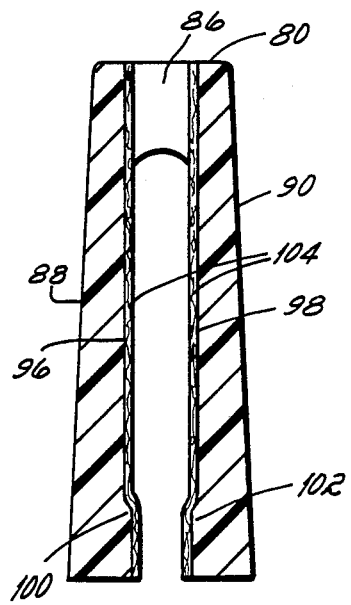
FIG. 4 is a cross sectional view of an alternative embodiment of the wedge element of this invention.

The block 38 and wedge element 74 are both preferably formed of a composite material such as a woven or unidirectional glass or graphite fiber impregnated with an epoxy matrix. If desired, the inner surfaces 96, 98 of sidewalls 76, 78 which contact the half pins 36 can be at least partially coated with a grit material such as silicon carbide having a high coefficient of friction. Additionally, as illustrated in FIG. 4, the inner surfaces 96, 98 may be covered with a deformable, elastic material such a "Kevlar" felt lining 104 impregnated with an epoxy matrix. The Kevlar felt lining 104 is a deformable, elastic material which at least partially conforms to the exterior surface of the half pins 36 when clamped thereto. This provides additional surface area of contact between the sidewalls 76, 78 and the half pins 36, which increases the frictional force therebetween. Although not illustrated in the drawings, the embodiment of wedge element 74 shown in FIG. 3 could also be provided with the "Kevlar" felt lining 104.

The pin clamp 34 of this invention functions as follows. The two half pins 36 shown in the figures are first inserted in the distal segment 12 of bone 18 and their outwardly extending ends are received within the elongated slots 84, 86 of wedge element 74 and elongated slots 56, 58 of block 38. See FIG. 2. The wedge element 74 is inserted by hand partially into the hollow interior 50 of block 38 until a flat head screw 106 inserted through the bore 52 in block 38 engages the threaded insert 92 in the top wall 80 of wedge element 74. The screw 106 seats within the recess 54 of bore 52 flush with the surface of top wall 48 and is rotated in one direction to pull or move the wedge element 74 upwardly into the hollow interior 50 of block 38 toward its top wall 48.

The outer surfaces 88, 90 of tapered sidewalls 76, 78 of wedge element 74 mate with the tapered inner surfaces 60, 62 of sidewalls 40, 42 of block 38. As the wedge element 74 moves upwardly within hollow interior 50, the sidewalls 76, 78 of wedge element 74 are forced inwardly toward one another by sidewalls 40, 42 of block 38 and exert a normal force against the half pins 36 positioned therebetween. These normal forces increase as the wedge element 74 moves upwardly in the hollow interior 50 to a maximum in the locked position shown in FIGS. 1 and 3 wherein the top wall 80 of wedge element 74 nearly engages the top wall 48 of block 38. During the movement of wedge element 74 into block 38, but prior to locking, the half pins 36 may be manipulated by the surgeon within slots 56, 58 and 84, 86 to apply a force between the threaded portion of pins 36 and the distal bone segment 12, which, in addition to screw threads of the pins 36, prevents loosening of the pins 36 from the distal bone segment 12. Once in the locked position shown in FIG. 3, the half pins 36 are securely gripped and fixed in place between the sidewalls 76, 78.

In a presently preferred embodiment, the taper angle of the block sidewalls 40, 42 and wedge element sidewalls 76, 78 is approximately 3° so that the wedge element 74 and block 38 are self-locking when joined together. The normal force exerted against the half pins 36 increases with lower taper angles, and progressively lesser normal forces are applied as the taper angle increases to 8°. Additionally, the wedge element 74 and block 38 are not self-locking as the taper angles increase beyond about 4° or 5°. If taper angles in excess of about 4° or 5° are employed, which facilitate removal of the wedge element 74 from block 38, the screw 106 is left in place within insert 92 to ensure that the wedge element 74 does not become loosened within the hollow interior 50 of block 38.

When the fracture 16 has sufficiently healed to permit removal of external fixation device 10, the pin clamp 34 releases the half pins 36 by rotating screw 106 in the opposite direction to force wedge element 74 outwardly from the hollow interior 50 of block 38.

While the invention has been described with reference to a preferred embodiment, it will be understood by those skilled in the art that various changes may be made and equivalents may be substituted for elements thereof without departing from the scope of the invention. In addition, many modifications could be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. In an external fixation device for positioning and immobilizing the distal segment and the proximal segment of a fractured bone to reduce the fracture, a clamping element adapted to clamp one end of pins inserted in the distal or proximal segments of the fractured bone comprising:

a block having opposed sidewalls and opposed endwalls each connected to a top wall forming a hollow interior, said sidewalls each being formed with a tapered inner surface, said top wall being formed with at least one elongated slot adapted to receive pins;

a wedge element having opposed sidewalls connected to a top wall, said sidewalls of said wedge element each being formed with a tapered outer surface mateable with said tapered inner surfaces of said sidewalls of said block, said top wall of said wedge element being formed with at least one elongated slot adapted to receive pins;

said elongated slot formed in said top wall of each said block and said wedge element having a lateral dimension greater than the diameter of the pins inserted in the distal or proximal segments of the fractured bone to permit lateral movement of the pins within said elongated slots relative to said sidewalls of said block and said wedge element;

means carried by said block for moving said wedge element into said hollow interior of said block;

said tapered sidewalls of said wedge element being forced toward one another upon contact with said mating, tapered sidewalls of said block to clamp pins securely therebetween.

2. The clamping element of claim 1 in which said top wall of said block is formed with a bore and said top wall of said wedge element is formed with a bore which mounts an insert having internal threads, said means for moving said wedge element into said hollow interior of said block comprising a screw insertable through said bore in said block and into threaded engagement with said insert in said top wall of said wedge element, said wedge element being moved into said hollow interior of said block upon rotation of said screw in one direction and being moved outwardly from said hollow interior of said block upon rotation of said screw in the opposite direction.

3. The clamping element of claim 2 in which said insert is formed with a flange at one end having a bottom surface, said insert being positioned within said bore in said top wall of said wedge element so that said bottom surface of said flange engages said top wall.

4. The clamping element of claim 1 in which said tapered inner surfaces of said sidewalls of said block form a taper angle in the range of about 2° to 8°, and said outer surfaces of said sidewalls of said wedge element form a taper angle in the range of about 2° to 8°.

5. The clamping element of claim 4 in which said taper angle of said sidewalls of said block and said taper angle of said sidewalls of said wedge element is approximately 3° to retain said block and said wedge element in assembled relation independently of said means for moving said wedge element into said hollow interior of said block.

6. In an external fixation device for positioning and immobilizing the distal segment and the proximal segment of a fractured bone to reduce the fracture, a clamping element adapted to clamp one end of pins inserted in the distal or proximal segments of the fractured bone comprising:

a block having opposed sidewalls and opposed endwalls each connected to a top wall forming a hollow interior, said sidewalls each being formed with a tapered inner surface, said top wall of said block being formed with at least one elongated slot adapted to receive pins;

a wedge element having opposed sidewalls connected to a top wall, said sidewalls of said wedge element each being formed with an inner surface at least partially covered with a grit material having a high coefficient of friction for engaging pins, and tapered outer surface mateable with said tapered inner surfaces of said sidewalls of said block, said top wall of said wedge element being formed with at least one elongated slot adapted to receive pins;

said elongated slot formed in said top wall of each said block and said wedge element having a lateral dimension greater than the diameter of the pins inserted in the distal or proximal segments of the fractured bone to permit lateral movement of the pins within said elongated slots relative to said sidewalls of said block and said wedge element;

means carried by said block for moving said wedge element into said hollow interior of said block;

said tapered sidewalls of said wedge element being forced toward one another upon contact with said mating, tapered sidewalls of said block to clamp pins securely therebetween.

7. The clamping element of claim 6 in which said inner surface of each of said sidewalls is formed with a stepped portion extending inwardly toward one another.

8. The clamping element of claim 6 in which said inner surface of said sidewalls is at least partially covered with a layer of lining material having a lower modulus of elasticity than said sidewalls, said lining material at least partially conforming to the shape of the outer surface of the pins to increase the surface area for gripping thereof.

9. The clamping element of claim 8 in which said lining material is at least partially covered with a grit material having a high coefficient of friction.

10. The clamping element of claim 6 in which said top walls of each said block and said wedge element are formed with a bore and two elongated slots one on either side of said bore.

* * * * *

UNITED STATES PATENT AND TRADEMARK OFFICE
CERTIFICATE OF CORRECTION

PATENT NO.   :   4,757,809

DATED        :   July 19, 1988

INVENTOR(S)  :   James B. Koeneman et al

It is certified that error appears in the above-identified patent and that said Letters Patent is hereby corrected as shown below:

In column 4, line 53, delete "4,584,995" and insert --4,747,400--.

In column 4, line 68, delete "cramp-" and insert --clamp---.

Signed and Sealed this

Thirteenth Day of December, 1988

Attest:

DONALD J. QUIGG

*Attesting Officer*          *Commissioner of Patents and Trademarks*